(12) United States Patent
Imhof et al.

(10) Patent No.: US 8,977,883 B2
(45) Date of Patent: Mar. 10, 2015

(54) TIME SYNCHRONIZATION IMPROVEMENTS FOR INTEROPERABLE MEDICAL DEVICES

(71) Applicants: Roche Diagnostics International AG, Rotkeuz (CH); Roche Diagnostics Operations, Inc., Indianapolis, IN (US)

(72) Inventors: Erich Imhof, Utzenstorf (CH); Guido Konrad, Bern (CH); James R. Long, Fishers, IN (US); Phillip E. Pash, Indianapolis, IN (US); Robert E. Reinke, Indianapolis, IN (US)

(73) Assignees: Roche Diagnostics Operations, Inc., Indianapolis, IN (US); Roche Diagnostics International AG, Rotkreuz (CH)

( * ) Notice: Subject to any disclaimer, the term of this patent is extended or adjusted under 35 U.S.C. 154(b) by 317 days.

(21) Appl. No.: 13/681,693

(22) Filed: Nov. 20, 2012

(65) Prior Publication Data
US 2014/0142540 A1    May 22, 2014

(51) Int. Cl.
*G06F 17/00* (2006.01)
*G06F 1/12* (2006.01)
*A61M 5/172* (2006.01)
*G06F 19/00* (2011.01)

(52) U.S. Cl.
CPC ......... *A61M 5/1723* (2013.01); *G06F 19/3412* (2013.01); *G06F 19/3468* (2013.01)
USPC ............... 713/401; 713/400; 607/27; 607/32; 607/59; 607/60

(58) Field of Classification Search
USPC ................... 713/400–401; 607/27, 32, 59–60
See application file for complete search history.

(56) References Cited

U.S. PATENT DOCUMENTS

| 7,079,977 | B2 * | 7/2006 | Osorio et al. .................. 702/176 |
| 7,187,979 | B2 * | 3/2007 | Haubrich et al. ............... 607/60 |
| 8,092,428 | B2 | 1/2012 | Ramey et al. |
| 8,117,481 | B2 | 2/2012 | Anselmi et al. |
| 8,118,770 | B2 | 2/2012 | Galley et al. |
| 8,260,398 | B2 * | 9/2012 | Uchiyama et al. ............. 600/424 |
| 8,396,563 | B2 * | 3/2013 | Reinke et al. .................... 607/60 |

(Continued)

FOREIGN PATENT DOCUMENTS

EP            0702464 A1    3/1996
WO    WO-2012154335 A2    11/2012

OTHER PUBLICATIONS

IBM Technical Disclosure Bulletin, vol. 33, No. 3B (1990).

(Continued)

*Primary Examiner* — M Elamin
(74) *Attorney, Agent, or Firm* — Harness, Dickey & Pierce, P.L.C.

(57) ABSTRACT

A computer-implemented method is presented for synchronizing time between two handheld medical devices that interoperate with each other. The method includes: determining a first time as measured by a first clock residing in the first medical device; determining a second time as measured by a second clock residing in a second medical device; evaluating whether the first clock is synchronized with the second clock; determining whether at least one of the first clock and the second clock was set manually by a user; and setting time of the first clock in accordance with the second time when the second clock was set manually by the user.

18 Claims, 8 Drawing Sheets

(56) References Cited

U.S. PATENT DOCUMENTS

| | | | |
|---|---|---|---|
| 2004/0215272 A1* | 10/2004 | Haubrich et al. | 607/27 |
| 2009/0081951 A1* | 3/2009 | Erdmann et al. | 455/41.2 |
| 2010/0160860 A1 | 6/2010 | Celentano et al. | |
| 2010/0265931 A1* | 10/2010 | Loc | 370/338 |
| 2011/0124996 A1 | 5/2011 | Reinke et al. | |
| 2011/0190850 A1* | 8/2011 | Reinke et al. | 607/60 |
| 2012/0263218 A1* | 10/2012 | Dal Molin et al. | 375/224 |
| 2014/0228913 A1* | 8/2014 | Molin et al. | 607/60 |

OTHER PUBLICATIONS

IEEE Transactions on communications, vol. 39, No. 10 (1991).
ISPCS 2009 International IEEE Symposium on Precision Clock Synchronization for Measurement, Control and Communication, (2009).
Journal of Computers, vol. 1, No. 5, pp. 20-29 (2006).
Local and metropolitan area networks, pp. 1-6, XP010854276 (2005).

* cited by examiner

TIME SYNCHRONIZATION IMPROVEMENTS FOR INTEROPERABLE MEDICAL DEVICES

FIELD

The present disclosure relates to improved methods for synchronizing time between two handheld medical devices that interoperate with each other, such as a diabetes management device and an insulin pump.

BACKGROUND

Diabetes mellitus is a chronic condition in which a person has elevated blood glucose levels that result from defects in the body's ability to produce and/or use insulin. For people with diabetes, successful management requires monitoring blood glucose changes. Regular testing of blood glucose levels can be an important part of diabetes management as a way to track changes throughout the day. For example, portable handheld medical diagnostic devices are often employed to measure concentrations of biologically significant components of bodily fluids, such as, for example, glucose concentration in blood. To test glucose with a glucose meter, a small sample of blood may be placed on a disposable test strip. A portable handheld glucose meter may include a strip port that receives the disposable test strip. The test strip may be coated with chemicals (glucose oxidase, dehydrogenase, or hexokinase) that combine with glucose in blood allowing it to measure the concentration of glucose in the blood sample. The portable handheld glucose meter then displays the glucose concentration as a number (or glucose measurement value).

Management of diabetes is complex as the level of blood glucose entering the bloodstream is dynamic. Blood glucose levels are sensitive to diet and exercise, but also can be affected by sleep, stress, smoking, travel, illness, menses, and other psychological and lifestyle factors unique to individual patients. Insulin in the bloodstream controls the transport of glucose out of the bloodstream and can also vary over time. The dynamic nature of blood glucose and insulin, and all other factors affecting blood glucose, often require a person with diabetes to forecast blood glucose levels and administer insulin throughout the day. Insulin pumps are one means for administering insulin to persons with diabetes.

More recently, handheld glucose meters and insulin pumps operate cooperatively with each other to manage diabetes care of persons with diabetes. For example, the handheld glucose meter may operate to measure current blood glucose levels of the person and formulate a recommended dosage of insulin as treatment. Such insulin recommendations may be based on previous blood glucose measures stored by the glucose meter as well as previous amounts of insulin administered and stored by the insulin pump. Amounts of insulin administered to the patient may be communicated by the insulin pump to the handheld glucose meter. The handheld glucose meter may in turn issue commands to the insulin pump to deliver insulin. This type of interaction illustrates the need for synchronization of the system clocks maintained by the two handheld medical devices.

This section provides background information related to the present disclosure which is not necessarily prior art.

SUMMARY

A computer-implemented method is presented for synchronizing time between two handheld medical devices that interoperate with each other. The method includes: determining a first time as measured by a first clock residing in the first medical device; determining a second time as measured by a second clock residing in a second medical device; evaluating whether the first clock is synchronized with the second clock; determining whether at least one of the first clock and the second clock was set manually by a user; and setting time of the first clock in accordance with the second time when the second clock was set manually by the user.

In one aspect of this disclosure, the time synchronization techniques are applied to a diabetes management device and an insulin pump that interoperate with each other. The method includes: determining, by the diabetes management device, a first time as measured by a first clock residing in the diabetes management device; retrieving, by the diabetes management device, a second time, via the wireless data link, from the insulin pump, the second time measured by a second clock residing in the insulin pump; computing, by the diabetes management device, a difference between the first time and the second time; retrieving, by the diabetes management device, a log of events occurring on the insulin pump, via the wireless data link, from the insulin pump; determining, by the diabetes management device, whether at least one of the first clock and the second clock was set manually by a user, the determination based in part on entries in the log retrieved from the insulin pump; and setting, by the diabetes management device, time of the first clock in accordance with the second time, the setting occurring in response to a determination that the difference exceeds a minimum threshold value and the second clock was set manually by the user. The method may further include: establishing, by the diabetes management device, the wireless data link with the insulin pump; and requesting, by the diabetes management device, the second time, via the wireless data link, from the insulin pump.

In response to a determination that the first clock was set manually by the user more recently than the second clock, sending, by the diabetes management device, a request to update the second clock via the wireless data link to the insulin pump.

In one aspect, the method includes creating, by the diabetes management device, an entry in the log for each occurrence of the time being reset on the first clock, where the determination of whether at least one of the first clock and the second clock was set manually is based in part on entries in the log of events maintained by the diabetes management device.

In response to a determination that only the second clock was set manually by the user, the first clock is set in accordance with the second time. The first clock is also set in accordance with the second time in response to a determination that the second clock was set manually by the user more recently than the first clock was set manually by the user.

In response to a determination that the difference between the first time and the second time exceeds a maximum threshold value which is larger than the minimum threshold value, prompting, by the diabetes management device, a user to input current time and setting, by the diabetes management device, time of the first clock to the current time input by the user.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

Figure 1:
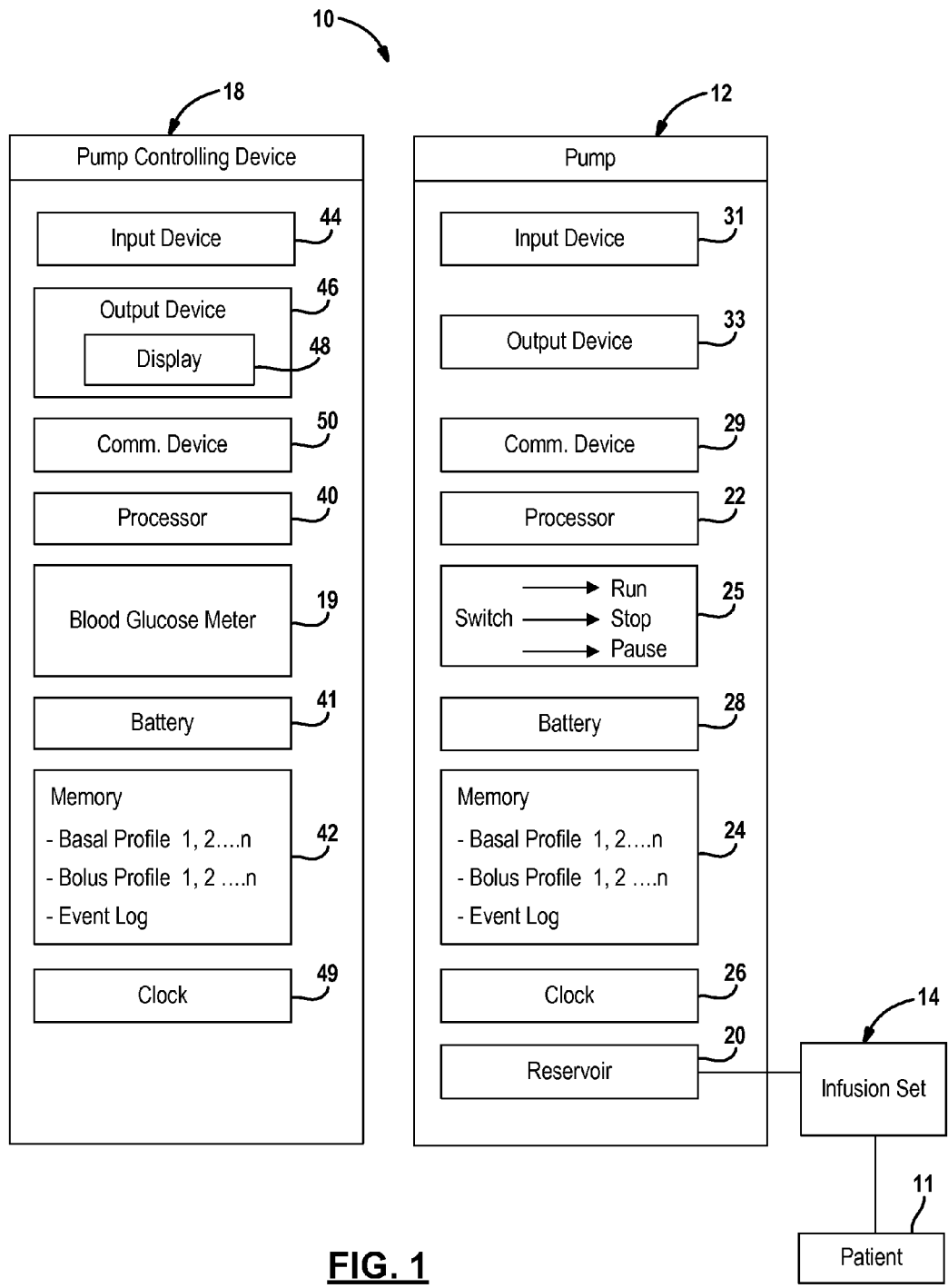
FIG. 1 is a schematic illustration of a diabetes treatment system according to various exemplary embodiments of the present disclosure.

The drawings described herein are for illustrative purposes only of selected embodiments and not all possible implementations, and are not intended to limits the scope of the present disclosure. Corresponding reference numerals indicate corresponding parts throughout the several views of the drawings.

DETAILED DESCRIPTION

FIG. 1 depicts an exemplary system 10 for delivering controlled dosages of insulin to a patient 11. The system 10 can generally include an insulin pump 12, an infusion set 14, and a pump controlling device 18. In the embodiments shown in FIG. 3, the pump controlling device 18 is embodied on a handheld or otherwise portable blood glucose meter 19 and thus may be referred to more generally as a diabetes management device. The pump controlling device 18, however, could be separate from a blood glucose meter in some embodiments. While reference is made to a pump controlling device and an insulin pump, it is understood that the time synchronization techniques set forth below are applicable to other types of handheld and/or portable medical devices.

Figure 2:
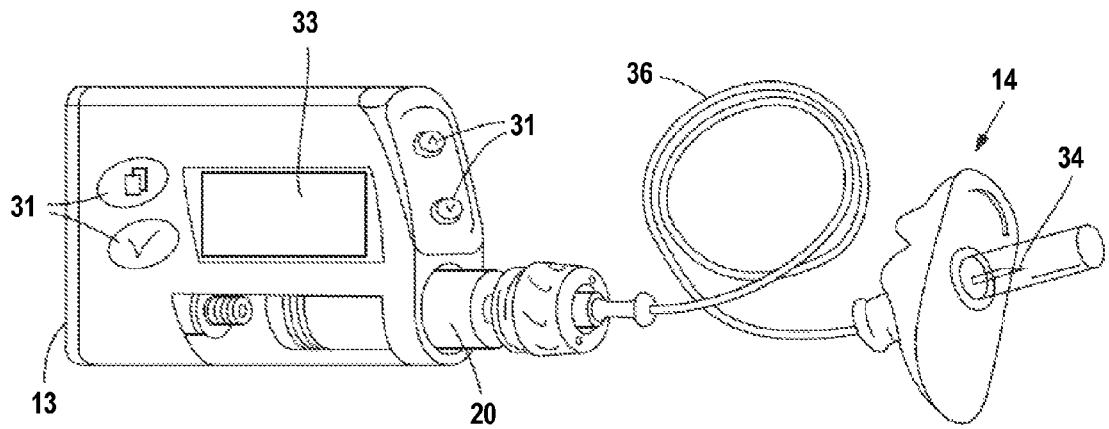
FIG. 2 is an isometric view of an insulin pump and an infusion set that can be implemented in the system of FIG. 1 according to exemplary embodiments of the present disclosure.

Referring to FIGS. 1 and 2, the insulin pump 12 can incorporate various features of a known, wearable, and portable insulin pump 12. Thus, the insulin pump 12 can include a housing 13 (FIG. 2) that supports at least one refillable reservoir 20 (i.e., insulin cartridge) containing insulin. (The reservoir 20 is shown partially removed from the housing 13 in FIG. 2.) The reservoir 20 can selectively deliver insulin to the infusion set 14 as will be described in greater detail below.

The pump 12 can also include a processor 22 (i.e., controller) that includes programmed logic and/or other elements for controlling the start and stop of insulin delivery from the reservoir 20, the flow rate of the insulin, etc. The pump 12 can additionally include one or more memory devices 24 (FIG. 1). The memory device 24 can store application programs and data and can be constructed of any suitable combination of volatile and/or nonvolatile memory. The memory device 24 can store an event log which contains entries for various types of events that occur on the pump. The memory device 24 can also store one or more predefined dosage schedules (i.e., dosage "profiles") that are tailored to the particular patient. In the embodiments illustrated in FIG. 1, the memory device 24 includes a plurality of different basal dosage profiles (indicated as "Basal Profile: 1, 2 . . . n"), and each of these profiles can dictate different basal dosage rates. The memory device 24 can also store one or more bolus dosage types (indicated as "Bolus Type: 1, 2 . . . n"), which can represent any number of standard bolus dosages, extended bolus dosages, combination bolus/multiwave bolus dosages, super bolus dosages, etc. As will be discussed, the processor 22 can access these profiles stored within the memory device 24 for controlling the amount of insulin delivered, the time of delivery, the rate of delivery, etc. It will be appreciated that the memory device 24 can store any number and type of dosage profile without departing from the scope of the present disclosure.

As shown in FIG. 1, the pump 12 can also include a switch, which is schematically illustrated and indicated at 25. The switch 25 can be used for changing the operating state of the pump 12 between two or more operating states. In the embodiments illustrated in FIG. 1, there are three operating states of the pump, RUN, STOP, and PAUSE. In the RUN mode, the pump 12 is able to deliver insulin, in the STOP mode, the pump 12 is unable to deliver insulin, and in the PAUSE mode, the pump 12 is temporarily unable to deliver insulin (e.g., due to the reservoir 20 being empty, etc.). It will be appreciated that the switch 25 can be substantially electrical (i.e., embodied as circuitry) as opposed to a mechanical switch with moving parts.

Also, the pump 12 can include a clock 26, which keeps track of the current date and time. By monitoring the clock 26, the processor 22 can track when insulin dosages are delivered. The memory device 24 can thus save the dosage amount, the dosage type, the dosage date and time, and other data related to insulin dosages delivered by the pump 12 for future reference.

Moreover, the pump 12 can include a power source, such as a battery 28, for providing power to the components of the pump 12. The battery 28 can include a main battery that supplies power for normal operations of the pump 12, and the battery 28 can include a backup battery that supplies power for only essential operations of the pump 12 when the main battery fails. It will be appreciated that the pump 12 can include additional or alternative power sources (e.g., one or more capacitors, etc.) without departing from the scope of the present disclosure.

Additionally, the pump 12 can include one or more input devices 31 that can be used by the patient 11 for inputting commands directly to the pump 12. As shown in FIG. 2, the input devices 31 can include one or more buttons that the patient 11 can depress for inputting such commands; however, the input device 31 could include a touch-sensitive surface, a sliding switch, or other input device. The pump 12 can further include one or more output devices 33 that can output one or more messages (e.g., messages relating to dosages, etc.). In the embodiments of FIG. 2, the output device 33 includes a display screen for outputting the messages visually; however, the output device 33 could include a speaker for outputting the messages aurally. Moreover, in some embodiments, the output device can include a tactile, vibrating motor for outputting the messages in a tactile manner.

The pump 12 can further include a communications device 29. The communication device 29 can establish communications between the pump 12 and the pump controlling device 18 as will be discussed in detail below. The communications device 29 can include a wireless transceiver (e.g., BLUETOOTH™ transceiver, etc.), and/or the communications device 29 can include a connector for connecting a wire between the pump 12 and the pump controlling device 18.

Furthermore, the infusion set 14 can be of a known type. Thus, the infusion set 14 can include a cannula 34 that is inserted subcutaneously into the patient 11 (i.e., the user, the person with diabetes). The infusion set 14 can also include a tube 36 that fluidly connects the cannula 34 to the reservoir 20 of the pump 12. As such, insulin can be delivered from the reservoir 20 and into the patient's bloodstream via the infusion set 14.

Figure 3:
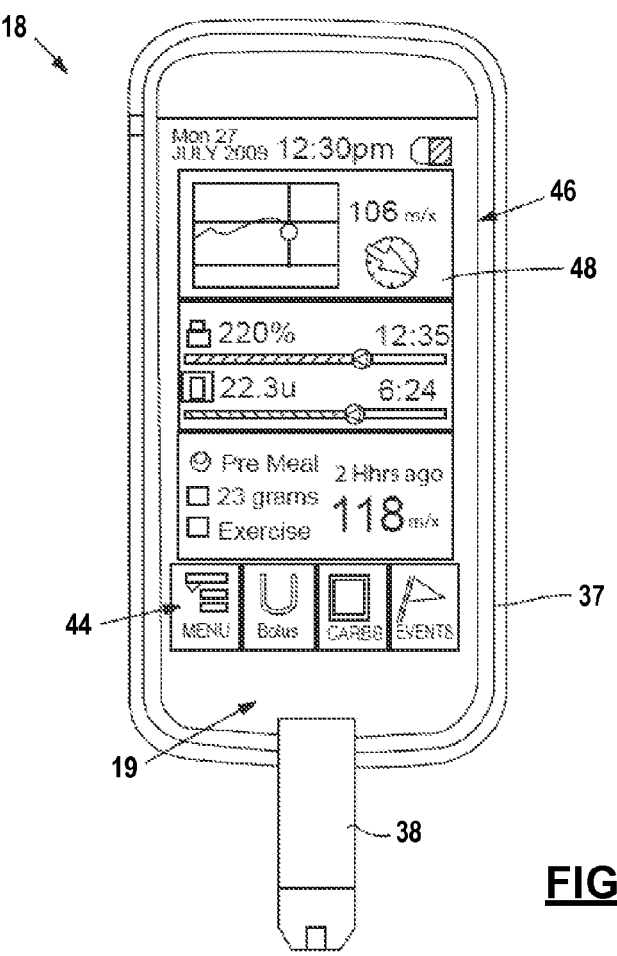
FIG. 3 is a front view of an exemplary diabetes management device that can be implemented in the system of FIG. 1 according to exemplary embodiments of the present disclosure.

Referring now to FIGS. 1 and 3, embodiments of the pump controlling device 18 will be discussed in detail. The pump controlling device 18 can include a housing 37 that houses the components of the device 18. As shown in FIG. 1, the pump controlling device 18 can include a processor 40, which can include programmed logic and/or other elements for controlling the device 18 and for sending control commands to the pump 12.

The device 18 can also include a memory device 42, which can store application programs and data and can be constructed of any suitable combination of volatile and/or non-volatile memory. As shown in FIG. 1, the memory device 42 can include basal and bolus profiles, which can be the same as those included on the memory device 24 of the pump 12. The memory device 42 can also include an event log which contains entries for various types of events that occur on the pump controlling device.

Moreover, the device 18 can include a battery 41 or other power source that supplies power to the components of the device 18. Also, the device 18 can include one or more input devices 44 with which the patient 11 can input commands. The input devices 44 can include buttons, switches, a touch sensitive surface, or any other suitable device. The device 18 can further include one or more output devices 46 that output information relating to operations of the system 10. The output devices 46 can be of any suitable type, such as a display 48 that outputs information visually, a speaker that outputs audible information, a vibrating motor that outputs tactile information, etc. In the embodiments of FIG. 3, the device 18 includes the display 48, and the display 48 includes one or more touch-sensitive areas, such that the display 48 can function as both an input device 44 and an output device 46. Also, as shown in FIG. 3, the display 48 can display various information, such as the current date and time, graphical information about insulin dosages, etc. Furthermore, the display 48 can display user selectable options for allowing the patient 11 to enter bolus information (labeled "Bolus" in FIG. 3), carbohydrate information (labeled "Carbs" in FIG. 3), or other information related to meals, exercise, periods of stress, physiological events such as menstruation, etc. (labeled "Events" in FIG. 3).

Also, as mentioned above, the pump controlling device 18 may include a blood glucose (bG) meter 19. The meter 19 can be of a known type for detecting the current (i.e., actual) blood glucose level of the patient 11. More specifically, the patient 11 can apply blood to a test strip 38 (FIG. 3), and the meter 19 can receive the strip 38 and detect the amount of glucose in the blood thereon. This information can be useful for calculating an appropriate bolus dosage or for other purposes. Also, this information can be stored in the memory device 42 in a suitable database for future analysis.

The blood glucose readings can also be associated or otherwise stored with other information in the memory device 42. For instance, the memory device 42 can store the blood glucose readings with other health related information of the particular patient 11. More specifically, the memory device 42 can store recommended bolus and carbohydrate advice history records. The memory device 42 can further store health, carbohydrate, and blood-glucose-related variables (e.g., insulin sensitivities of the patient 11 for particular time segments of particular days of the week, etc.).

The device 18 can include a clock 49, which keeps track of the current date and time. By monitoring the clock 49, the processor 40 can tag when blood glucose measures are taken by the patient as well as other data obtained and stored by the device.

The device 18 can further include a communication device 50, such as a wireless transceiver (e.g., a BLUETOOTH™ transceiver, etc.) or a connector for connecting a wire. Thus, the communication device 50 of the pump controlling device 18 can selectively communicate with the communication device 29 of the insulin pump 12 wirelessly and/or via a wired connection. As will be discussed, the communication devices 50, 29 can provide two-way communication between the pump controlling device 18 and the insulin pump 12.

Thus, the processor 40 can run software stored in the memory device 42. Also, various input commands can be provided from the patient 11 via the input device 44 (e.g., the touch-sensitive surface of the display 48) for performing various functions. For instance, the processor 40 can calculate a recommended meal bolus, a recommended correction bolus, a recommended total bolus, and/or a suggested carbohydrate amount in this manner. Also, the processor 40 can cause the communication device 50 to transmit various control commands to the pump 12. The pump controlling device 18 can send a variety of control commands, such as a START BOLUS DELIVERY, STOP PUMP, and other commands. The insulin amount, dosage time, insulin flow rate, etc. can also be specified in this command.

Figure 4:
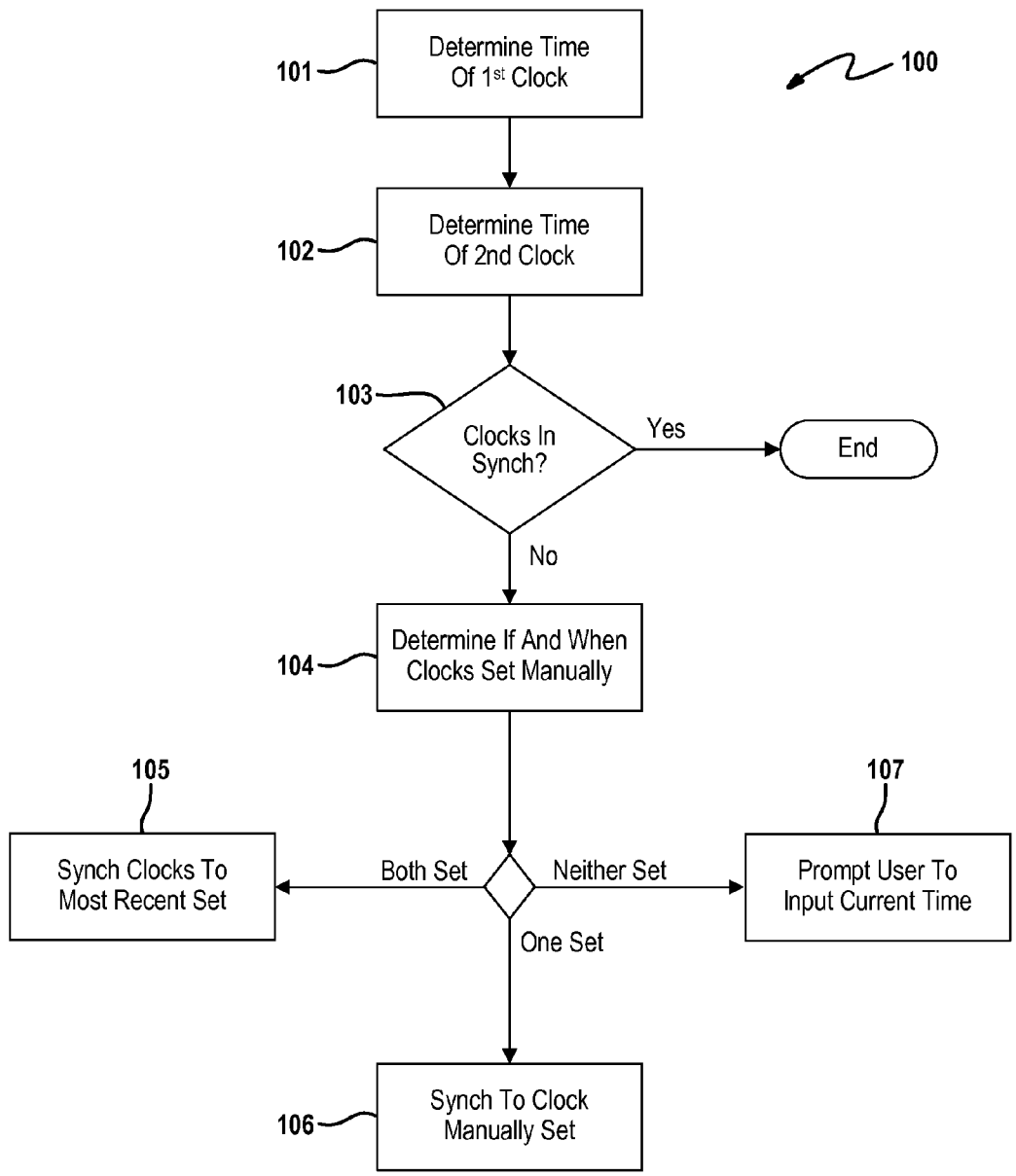
FIG. 4 is a flowchart depicting an improved method for synchronizing time between two handheld medical devices.

FIG. 4 provides an overview of an improved method 100 for synchronizing time between two handheld medical devices that interoperate with each other, such as a diabetes management device 18 and an insulin pump 12. Rather than designating any one device as controlling, the paradigm is shifted so that time synchronization is dictated by the user as further described below. While reference is made throughout this disclosure to handheld devices used in the treatment of diabetes care, it is readily understood that the time synchronization techniques set forth below may be extended to other types of medical devices that interoperate with each other.

Time synchronization begins at 101 by determining the time as measured by a first clock residing on a first medical device. The time as measured by a second clock residing on a second medical device is also determined at 102. Next, a determination is made at 103 as to whether the two clocks are out of synch with each other. For example, the clocks may be deemed out of synch when a difference between the two clocks exceeds a predefined threshold. Different scenarios which may cause the two clocks to be out of synch include but are not limited to the user changes the clock on one device only, the user changes the clocks on both devices independently, clocks on the two devices drift apart, the clock on one device only is reset automatically or the clocks on both devices are reset automatically. Other scenarios which may cause the clocks to become out of synch are also contemplated by this disclosure.

If the two clocks are deemed to be out of synch with each other, then a determination is made at 104 as to whether either the first clock or the second clock was set manually set by the user. This is important because if the manual setting occurred before the last synch time then any differences must be due to drift in one or both clocks and confidence is lost that the device that was set more recently is more likely accurate. Clocks on the two devices are in turn synchronized in accordance with this determination. In one embodiment, when the clocks on both devices have been set manually by the user, the clocks of the two devices will be synchronized to the clock that was most recently set by the user as indicated at 105. In some instances, the clock on only one of the two devices has been set manually by the user and thus the clock of the other device will be synchronized to the clock that has been set manually by the user as indicated at 106. In other instances, neither clock has been set manually by the user. In these instances, the user may be prompted to input the current time at 107 which is in turn used to update the clocks in both devices. No synchronization is needed so long as the two clocks remain in synch with each other.

Figure 5A:
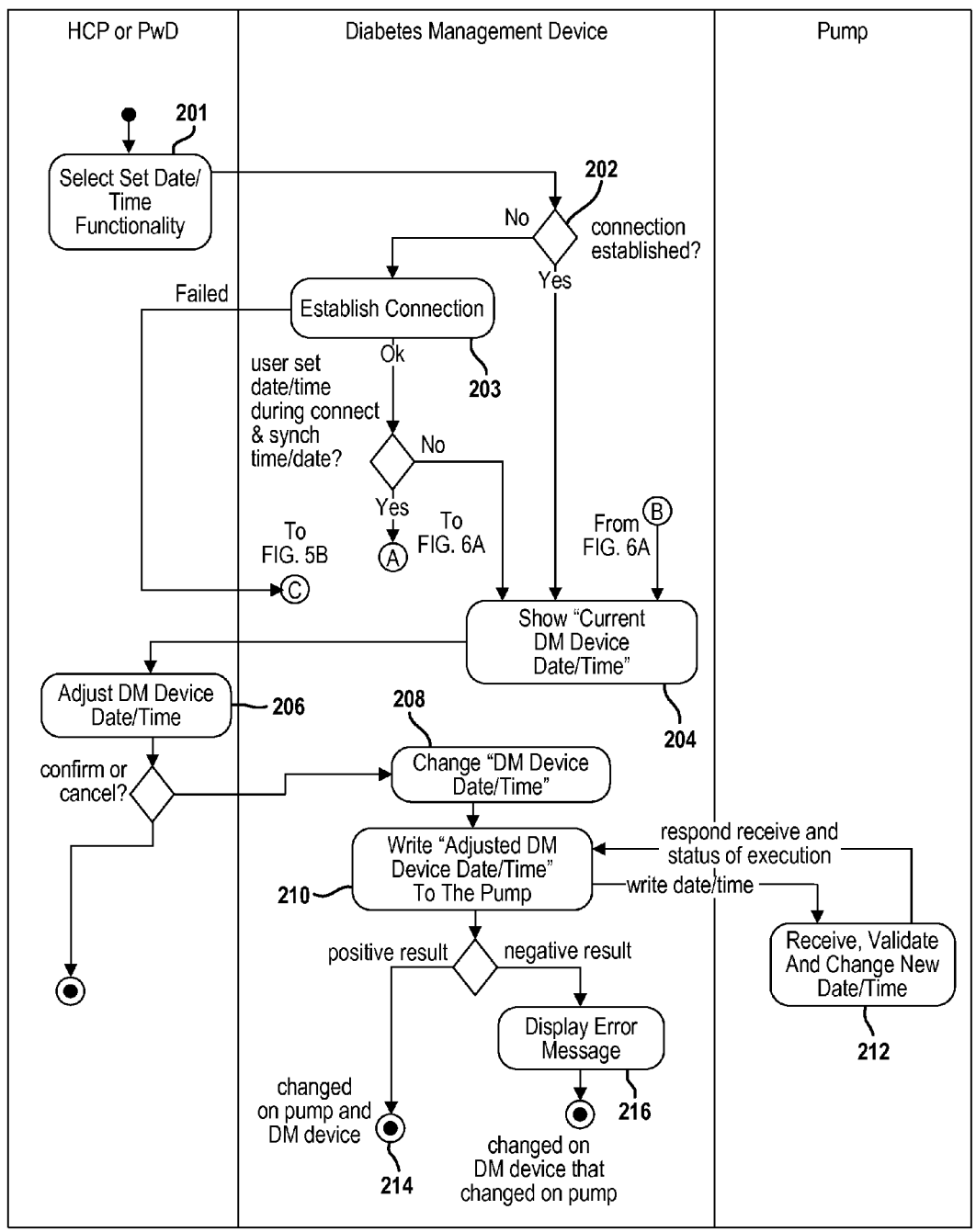
FIGS. 5A and 5B are an activity diagram for setting date and time of a handheld medical device.
Figure 5B:
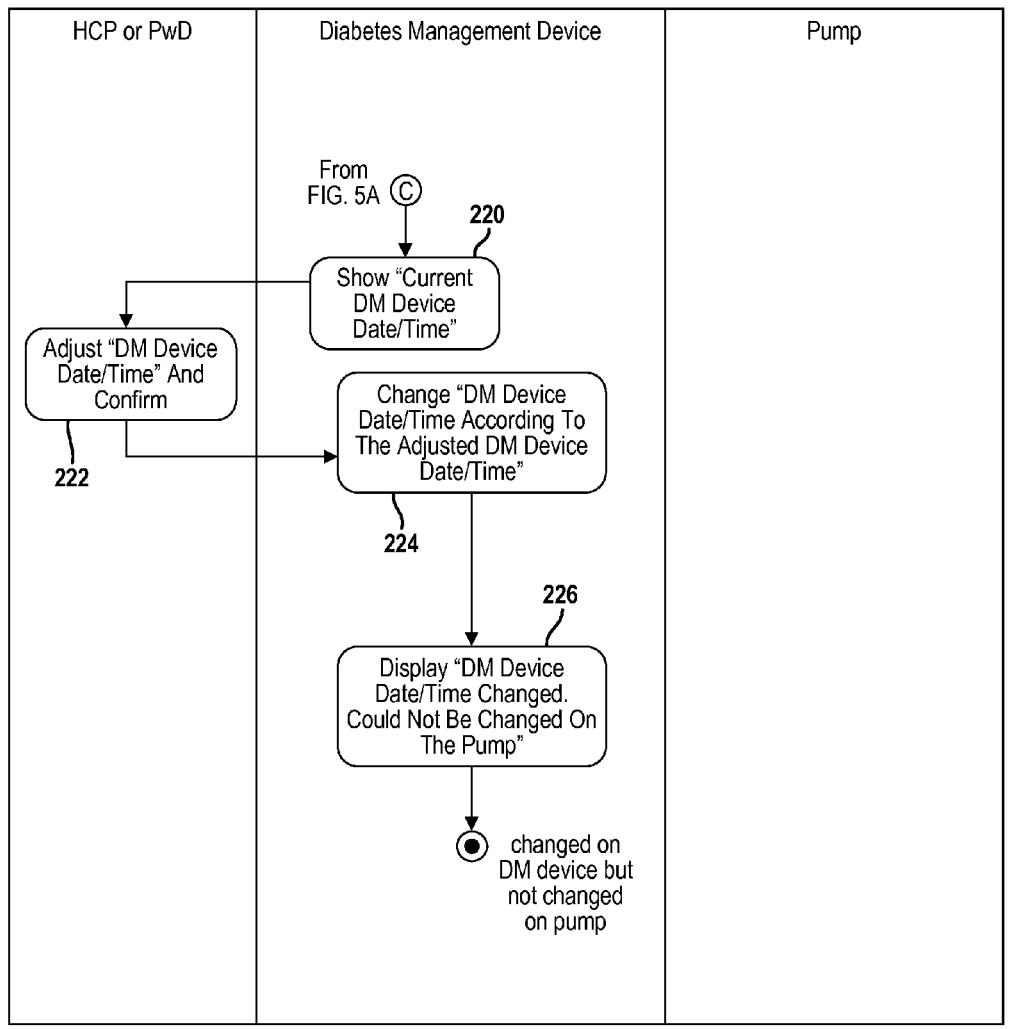

FIGS. 5A and 5B present an activity diagram for setting time between a handheld diabetes management device and an insulin pump. In an exemplary embodiment, the date and time can be set by a user interfacing with the diabetes management device as indicated at 201. It is envisioned that date and time can also be set by a user interfacing with the insulin pump. Therefore, functionality described below in the context of the diabetes management device may also be integrated into the insulin pump.

When a user attempts to set the date and time, the diabetes management device first checks at 202 whether a data connection has been established between the diabetes management device and an insulin pump. If a data connection has been established, the current date and time is displayed to the user at 204 by the diabetes management device. The date and/or time can be adjusted at 206, if necessary, by the user. Once the newly adjusted date and/or time has been confirmed by the user, the system date and time on the diabetes management device can be updated at 208 with the newly adjusted date and time. Additionally, the diabetes management device will attempt to update the system date and time kept by the insulin pump. To do so, a request to update the date and time is sent at 210 via the data connection to the insulin pump. In response to the request, the insulin pump will operate at 212 to update its system date and time with the newly adjusted date and time contained in the request sent by the diabetes management device. The insulin pump will then send a reply message via the data connection to the diabetes management device, where the reply message indicates whether the update was successfully completed. If the system date and time on the insulin pump was successfully updated, then an appropriate notification (e.g., "Date and time successfully updated") is provided at 214 to the user Likewise, an appropriate notification can be provided at 216 to the user if the update to the system date and time on the insulin pump was unsuccessful. For example, the notification may indicate that the system date and time was successfully updated on the diabetes management device but not on the insulin pump.

When a user attempts to set the date and time but a data connection has not yet been established with the insulin pump, the diabetes management device will try establishing a data connection as indicated at 203. If a data connection is established, the diabetes management device will verify that the date and time is synchronized between the two devices and, if applicable, synchronize the date and time as further described in relation to FIGS. 6A and 6B. If the diabetes management device is unable to establish a data connection with the insulin pump, then date and time may be updated only on the diabetes management device. To do so, the current date and time is displayed to the user at 220 by the diabetes management device. The date and/or time can be adjusted, if necessary, at 222 by the user. The system date and time on the diabetes management device is then updated at 224 with the newly adjusted date and time. Lastly, an appropriate notification can be provided to the user as indicated at 226. For example, the notification may indicate that the system date and time was successfully updated on the diabetes management device but not on the insulin pump.

Figure 6A:
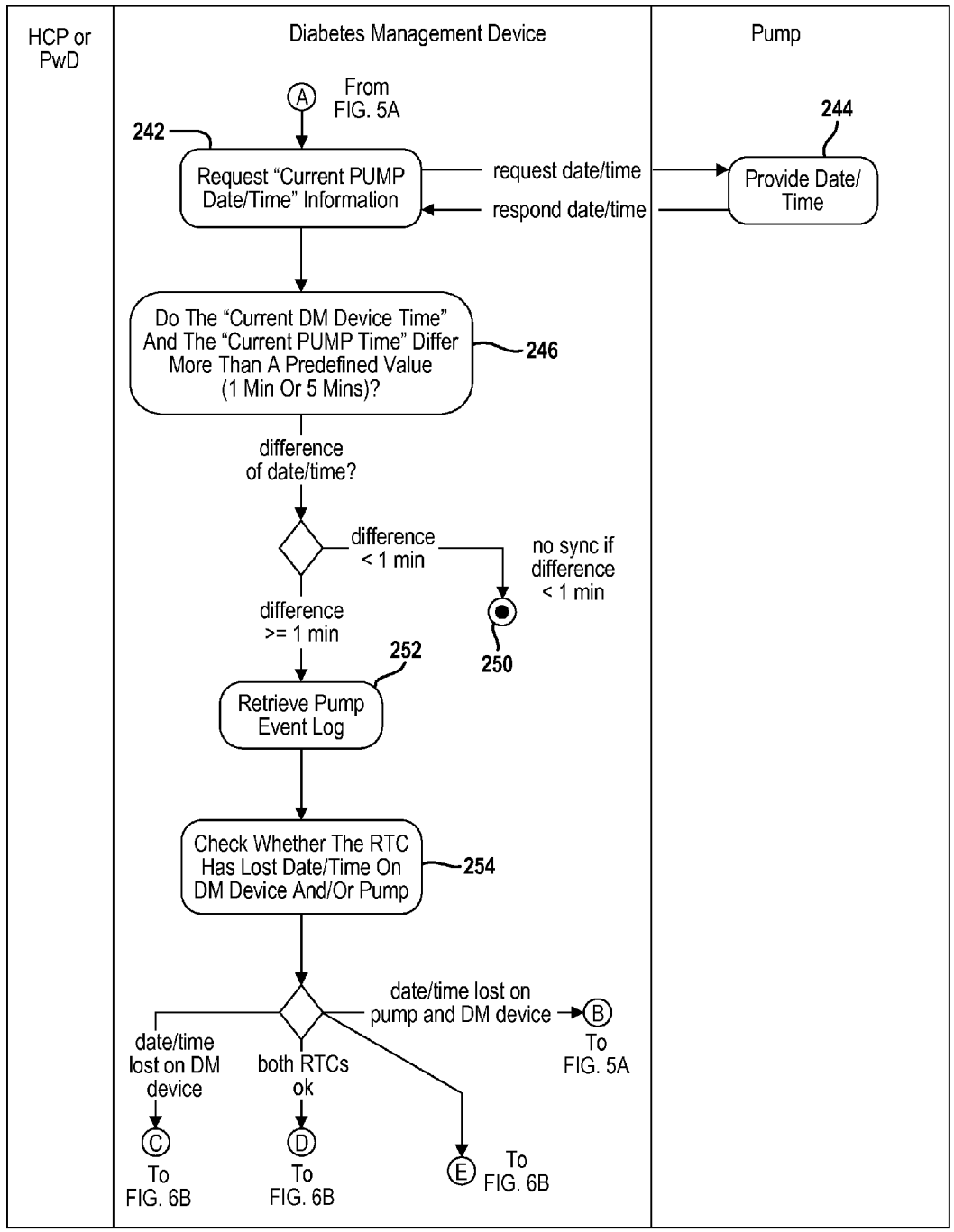
FIGS. 6A-6C are an activity diagram for synchronizing date and time between a pair of handheld medical devices.
Figure 6B:
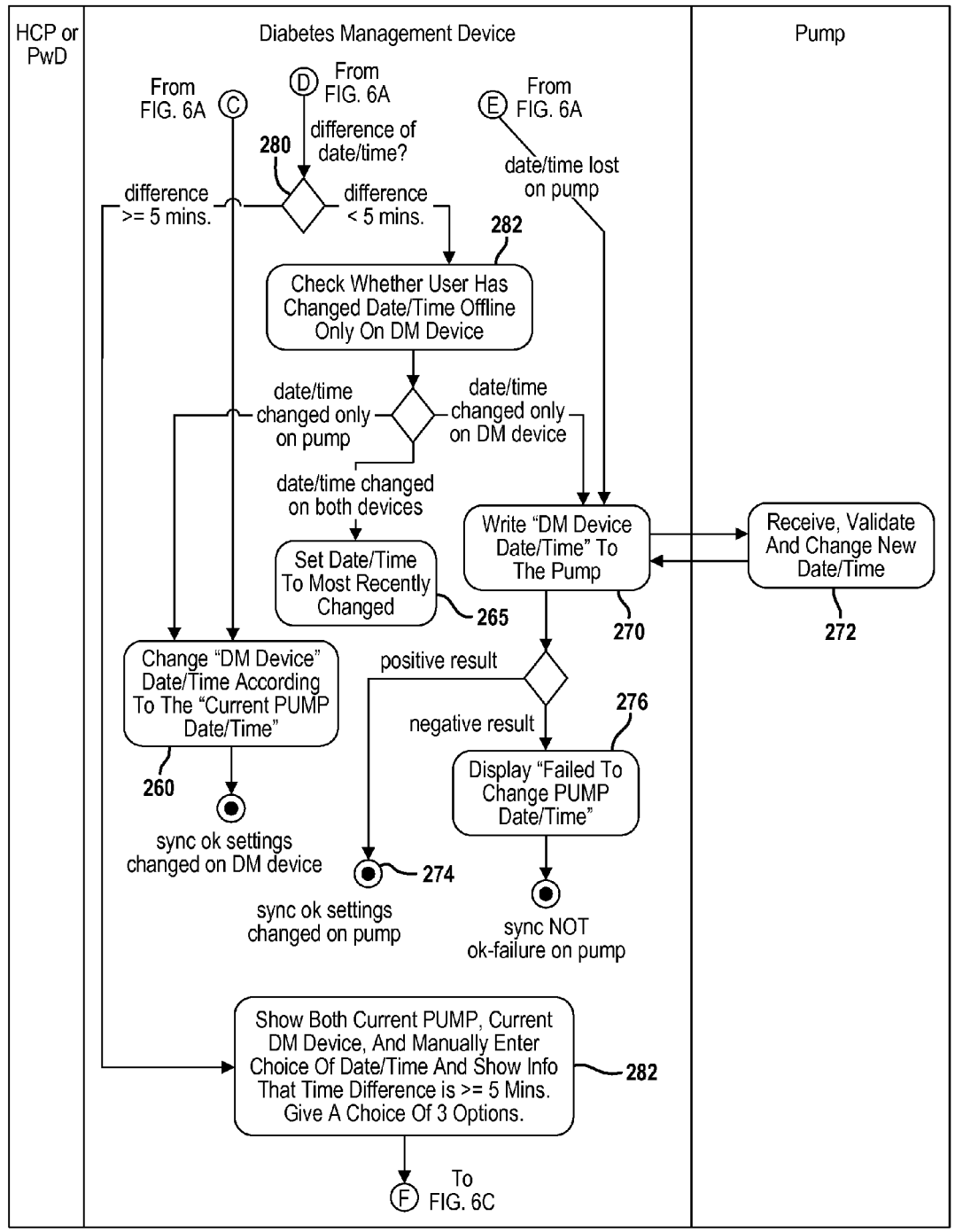
Figure 6C:
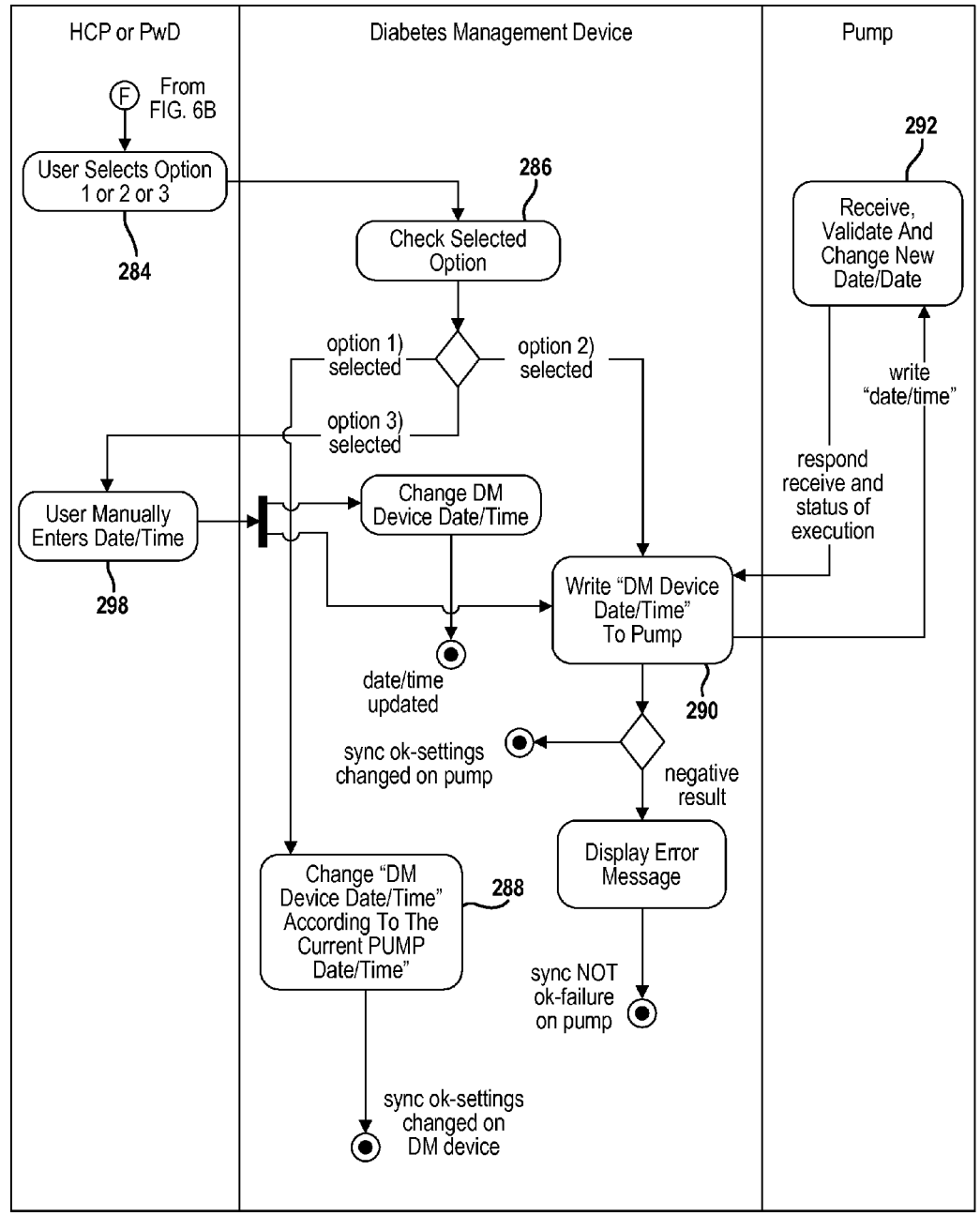

FIGS. 6A-6C depict an exemplary embodiment for synchronizing date and time once a data connection has been established between the diabetes management device and an insulin pump. In one embodiment, the synchronization process occurs each time a connection is established between the two devices. It is envisioned that the synchronization process may be initiated at other times, such as upon user request or occurrence of other types of triggering conditions.

Synchronization begins with the diabetes management device requesting system date and time from the insulin pump as indicated at 242. The request for the system date and time can be sent via the data connection established between the two devices. The insulin pump is configured to respond to the request as indicated at 244. Upon receipt of the current date and time from the pump, a difference is computed at 246 between the system date and time retrieved from the insulin pump and the system date and time kept by the diabetes management device. In one embodiment, synchronization between the two devices is needed when the difference exceeds a predefined minimum threshold (e.g., one minute). Conversely, there is no need to synchronize time between the two devices when the difference is less than the predefined minimum threshold as indicated at 250. In the context of other types of devices, it may be necessary to synchronize the time between the two devices more precisely.

To synchronization time between the two devices, a determination is made as to which device, if any, the system date and time was most recently set by the user. In an exemplary embodiment, this determination relies upon event logs maintained by each of the two devices. Each device can maintain a log of events occurring on the respective device. When a user manually sets or updates the clock on a given device, an entry is placed in the log, where the entry indicates that the clock has been set manually by the user. Each device can also be configured to create an entry in the log when the system date and time is lost or otherwise reset automatically by the device, for example, when the power source has been removed from the device. In this case, the entry in the event log indicates that the clock has been reset to a default time. Other types of scenarios for updating the clock are also contemplated and the devices can be configured to update the event log accordingly.

With continued reference to FIG. 6A, the event log is retrieved at 252 from the insulin pump. Event logs for each device can then be analyzed at 254. For each device, a determination is made from the entries in the respective event log as to how the clock was most recently updated. In one embodiment, the clock state is determined from the most recent entry pertaining to the clock as retrieved from the respective event log. For example, an entry can be created in the log for each occurrence of the clock being reset. In this way, the most recent entry in the log indicates the current clock state. Depending on the outcome, time between the two devices will be synchronized as described below.

System date and time for the diabetes management device will be changed to match the system date and time retrieved from the insulin pump as indicated at 260 when the system date and time on the diabetes management device was lost or otherwise reset automatically. In other words, since the system date and time on the insulin pump was set manually by the user while the system date and time on the diabetes management device was reset automatically, both devices will be synchronized to the system date and time of the insulin pump.

System date and time for the insulin pump should be changed to match the system date and time of the diabetes management device as indicated at 270 when the system date and time on the insulin pump was lost or otherwise reset automatically. More specifically, a request to update the date and time is sent by the diabetes management device via the data connection to the insulin pump. In response to the request, the insulin pump will operate at 272 to update its system date and time with the system date and time contained in the request sent by the diabetes management device. The insulin pump will then send a reply message via the data connection to the diabetes management device, where the reply message indicates whether the update was completed successfully. If the system date and time on the insulin pump was successfully updated, then an appropriate notification (e.g., "Date and time successfully updated") may be provided at 274 to the user. Likewise, an appropriate notification may be provided at 276 to the user if the update to the system date and time on the insulin pump was unsuccessful. In this case, the system date and time on the diabetes management device was set manually by the user while the system date and time on the insulin pump was reset automatically, both devices will be synchronized to the system date and time of the diabetes management device.

When the system date and time on both devices was reset automatically, the user can be prompted to input the current date and time. Processing may proceed at B of FIG. 5A as described above. In this case, the system date and time on both devices will be synchronized to the current date and time input by the user.

When the system date and time on both devices has been set manually by the user, the difference between the system date and time retrieved from the insulin pump and the system date and time kept by the diabetes management device is further evaluated at 280. If the difference is less than a predefined maximum threshold (e.g., five minutes), then time between the two devices may be synchronized in an automated manner. In one embodiment, a determination is made at 282 as to which device the system date and time has been set manually by the user. If the system date and time has been set manually by the user only on the diabetes management device, then a request to update the system date and time is sent at 270 by the diabetes management device to the insulin pump. If the system date and time has been set manually by the user only on the insulin pump, then the system date and time for the diabetes management device will be changed at 260 to match the insulin pump. In some cases, the system data and time has been manually updated on both the diabetes mangement device and the insulin pump. Entries in the event log may include timestamps indicating when the system date and time were updated by the user. System date and time for both devices can then be synchronized at 265 to the device whose clock was most recently set by the user.

On the other hand, if the difference is greater than the predefined maximum threshold, then it is preferable to prompt the user for further input. In one embodiment, system date and time from both the diabetes management device and the insulin pump are presented at 282 on a display of the diabetes management device. Additionally, the user may be presented at 284 with options for how best to synchronize time between the two devices. Options may include: (1) diabetes management device adopts system date and time from the insulin pump; (2) insulin pump adopts system date and time from the diabetes management device; and/or (3) user enters the current date and time manually. Upon receipt of the user selection at 286, time is synchronized on the two devices accordingly. That is, system date and time on the diabetes management device will be changed to match the system date and time retrieved from the insulin pump as indicated at 288 when the user selects option (1). System date and time for the insulin pump will be changed to match the system date and time of the diabetes management device as indicated at 290 when the user selects option (2). User is prompted at 298 to manually enter the current date and time when the user selects options (3). In either case, time is synchronized in accordance with the user's input.

The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are non-volatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and operations presented herein are not inherently related to any particular computer or other apparatus. Various general-purpose systems may also be used with programs in accordance with the teachings herein, or it may prove convenient to construct more specialized apparatuses to perform the required method steps. The required structure for a variety of these systems will be apparent to those of skill in the art, along with equivalent variations. In addition, the present disclosure is not described with reference to any particular programming language. It is appreciated that a variety of programming languages may be used to implement the teachings of the present disclosure as described herein.

The present disclosure is well suited to a wide variety of computer network systems over numerous topologies. Within this field, the configuration and management of large networks comprise storage devices and computers that are communicatively coupled to dissimilar computers and storage devices over a network, such as the Internet.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same can also be varied in many ways. Such variations are not to be regarded as a departure from the disclosure, and all such modifications are intended to be included within the scope of the disclosure.

What is claimed is:

1. A computer-implemented method for synchronizing time between two handheld medical devices that interoperate with each other, comprising:
    determining, by a first medical device, a first time as measured by a first clock residing in the first medical device;
    determining, by the first medical device, a second time as measured by a second clock residing in a second medical device;
    evaluating, by the first medical device, whether the first clock is synchronized with the second clock;
    determining, by the first medical device, whether at least one of the first clock and the second clock was set manually by a user, the determination in response to an evaluation that the first clock is not synchronized with the second clock; and
    setting, by the first medical device, time of the first clock in accordance with the second time, the setting occurring in response to a determination that the second clock was set manually by the user.

2. The computer-implemented method of claim 1 further comprises
    establishing, by the first medical device, a data connection with the second medical device; and
    requesting, by the first medical device, the second time, via the data connection, from the second medical device.

3. The computer-implemented method of claim 2 further comprises sending, by the first medical device, a request to update the second clock via the data connection to the second medical device, the sending occurring in response to a determination that the first clock was set manually by the user more recently than the second clock.

4. The computer-implemented method of claim 2 further comprises
    determining, by the first medical device, a difference between the first time and the second time; and
    setting, by the first medical device, time of the first clock in accordance with the second time, the setting occurring in response to a determination that the second clock was set manually by the user more recently than the first clock and the difference exceeds a minimum threshold value but is less than a maximum threshold value.

5. The computer-implemented method of claim 4 further comprises
    prompting, by the first medical device, a user to input current time, the prompting occurring in response to a determination that the difference exceeds the maximum threshold value; and
    setting, by the first medical device, time of the first clock to the current time input by the user.

6. The computer-implemented method of claim 5 further comprises sending, by the first medical device, a request to update to the second clock, via the data connection, to the second medical device.

7. The computer-implemented method of claim 1 further comprises
    maintaining, by the first medical device, a log of events occurring on the first medical device;
    creating, by the first medical device, an entry in the log for each occurrence of the time being reset on the first clock; and
    evaluating, by the first medical device, entries in the log to determine whether at least one of the first clock and the second was set manually by the user.

8. A computer-implemented method for synchronizing time between a handheld diabetes management device and an insulin pump that interoperate with each other via a wireless data link, comprising:
    determining, by the diabetes management device, a first time as measured by a first clock residing in the diabetes management device;
    retrieving, by the diabetes management device, a second time, via the wireless data link, from the insulin pump, the second time measured by a second clock residing in the insulin pump;
    computing, by the diabetes management device, a difference between the first time and the second time;
    retrieving, by the diabetes management device, a log of events occurring on the insulin pump, via the wireless data link, from the insulin pump;
    determining, by the diabetes management device, whether at least one of the first clock and the second clock was set manually by a user, the determination based in part on entries in the log retrieved from the insulin pump; and
    setting, by the diabetes management device, time of the first clock in accordance with the second time, the setting occurring in response to a determination that the difference exceeds a minimum threshold value and the second clock was set manually by the user.

9. The computer-implemented method of claim 8 further comprises
    establishing, by the diabetes management device, the wireless data link with the insulin pump; and
    requesting, by the diabetes management device, the second time, via the wireless data link, from the insulin pump.

10. The computer-implemented method of claim 9 further comprises sending, by the diabetes management device, a request to update the second clock via the wireless data link to the insulin pump, the sending occurring in response to a determination that the first clock was set manually by the user more recently than the second clock.

11. The computer-implemented method of claim 8 further comprises creating, by the diabetes management device, an entry in the log for each occurrence of the time being reset on the first clock, where the determination of whether at least one of the first clock and the second clock was set manually is based in part on entries in the log of events maintained by the diabetes management device.

12. The computer-implemented method of claim 11 further comprises creating, by the diabetes management device, an entry in the log when the first clock is updated automatically by the diabetes management device.

13. The computer-implemented method of claim 8 wherein setting the first clock in accordance with the second time occurs in response to a determination that only the second clock was set manually by the user.

14. The computer-implemented method of claim 8 wherein setting the first clock in accordance with the second time occurs in response to a determination that the second clock was set manually by the user more recently than the first clock was set manually by the user.

15. The computer-implemented method of claim 8 further comprises sending, by the diabetes management device, a request to update to the second clock, via the wireless data link, to the insulin pump, the sending occurring in response to a determination that only the first clock was set manually by the user.

16. The computer-implemented method of claim 8 further comprises
    prompting, by the diabetes management device, a user to input current time, the prompting occurring in response to a determination that the difference exceeds a maximum threshold value which is larger than the minimum threshold value; and
    setting, by the diabetes management device, time of the first clock to the current time input by the user.

17. The computer-implemented method of claim 16 further comprises sending, by the diabetes management device, a request to update to the second clock, via the wireless data link, to the insulin pump.

18. The computer-implemented method of claim 8 further comprises
    sending, by the diabetes management device, a request to update to the second clock, via the wireless data link, to the insulin pump, the sending occurring in response to a determination that only the first clock was set manually by the user.

* * * * *